United States Patent [19]

Ramaiah

[11] Patent Number: 6,143,723
[45] Date of Patent: Nov. 7, 2000

[54] PIGMENTORY AGENT

[76] Inventor: Abburi Ramaiah, 137 Charak Sadan, Vikas Puri, New Delhi-110018, India

[21] Appl. No.: 08/855,958

[22] Filed: May 14, 1997

[30] Foreign Application Priority Data

May 20, 1996 [IN] India ............................... 1051/DEL/96
May 20, 1996 [IN] India ............................... 1052/DEL/96

[51] Int. Cl.$^7$ .................................. A61K 38/18
[52] U.S. Cl. .................. 514/21; 514/2; 514/13; 514/14; 514/15; 514/16; 514/946; 514/947; 514/844; 424/49; 424/401; 424/78.02; 424/78.03; 424/78.06
[58] Field of Search ................... 514/2, 21, 13, 514/14, 15, 16, 946, 947, 844; 530/399, 300; 424/59, 401, 78.02, 78.03, 78.06

[56] References Cited

U.S. PATENT DOCUMENTS

| | | | |
|---|---|---|---|
| 5,132,408 | 7/1992 | Baird et al. | 530/399 |
| 5,217,954 | 6/1993 | Foster et al. | 514/12 |
| 5,252,718 | 10/1993 | Baird et al. | 530/399 |
| 5,288,704 | 2/1994 | Ungheri et al. | 514/12 |
| 5,492,894 | 2/1996 | Bascom et al. | 514/18 |
| 5,514,652 | 5/1996 | Watanuki et al. | 514/12 |

FOREIGN PATENT DOCUMENTS

| | | |
|---|---|---|
| 05043424 | 2/1993 | Japan . |
| 05043442 | 2/1993 | Japan . |
| 91/07982 | 6/1991 | WIPO . |

OTHER PUBLICATIONS

Halaban et al. "bFGF is the putative natural growth factor for human melanocytes," In Vitro Cell. Develop. Biol. (1987) 23(1): 47–52.
Baird et al. "Receptor– and heparin–binding domais of basic fibrolast growth factor," Proc. Natl. Acad. Sci. (1988) 85: 2324–28, Apr. 1988.
Puri et al. "Basic fibroblast growth factor promotes melanin synthesis by melanocytes," Arch. Dermatolog. Res. (1996) 288: 633–35, Oct. 1996.
Strianse, S.J. in "Cosmetics: Science and Technology," Balsam, Ed. vol. 1 (1972) (Wiley: NY) p. 179–222.
"Remington's Pharmaceutical Sciences" Gennaro, Ed. (1990) (Mack Pub. Company: Easton, PA) p. 1519–1544.

*Primary Examiner*—Jean C. Witz
*Attorney, Agent, or Firm*—Venable; George H. Spencer

[57] ABSTRACT

This invention relates to a pigmentary agent for treatment of pigmentary isorers an also to a cosmetic preparation. Such a preparation does not require any exposure of the skin surface to sunlight. The invention also relates to a vehicle for peptides having a molecular weight of up to 1500.

17 Claims, 7 Drawing Sheets

SEQUENCE LISTING

<160> NUMBER OF SEQ ID NOS: 9

<210> SEQ ID NO 1
<211> LENGTH: 10
<212> TYPE: PRT
<213> ORGANISM: Unknown
<220> FEATURE:
<223> OTHER INFORMATION: Description of Unknown Organism: bFGF fragment

<400> SEQUENCE: 1

Tyr Arg Ser Arg Lys Tyr Ser Ser Trp Tyr
1            5                10

<210> SEQ ID NO 2
<211> LENGTH: 10
<212> TYPE: PRT
<213> ORGANISM: Unknown
<220> FEATURE:
<223> OTHER INFORMATION: Description of Unknown Organism: bFGF fragment

<400> SEQUENCE: 2

Tyr Arg Ser Arg Lys Tyr Glu Ser Trp Tyr
1            5                10

<210> SEQ ID NO 3
<211> LENGTH: 10
<212> TYPE: PRT
<213> ORGANISM: Unknown
<220> FEATURE:
<223> OTHER INFORMATION: Description of Unknown Organism: bFGF fragment
<220> FEATURE:
<223> OTHER INFORMATION: cyclo peptide

<400> SEQUENCE: 3

Tyr Arg Ser Arg Lys Tyr Glu Ser Trp Tyr
1            5                10

<210> SEQ ID NO 4
<211> LENGTH: 11
<212> TYPE: PRT
<213> ORGANISM: Unknown

```
<220> FEATURE:
<223> OTHER INFORMATION: Description of Unknown Organism: bFGF fragment
<220> FEATURE:
<223> OTHER INFORMATION: cyclo peptide

<400> SEQUENCE: 4

Gly Tyr Arg Ser Arg Lys Tyr Ser Ser Arg Tyr
1               5                  10

<210> SEQ ID NO 5
<211> LENGTH: 15
<212> TYPE: PRT
<213> ORGANISM: Unknown
<220> FEATURE:
<223> OTHER INFORMATION: Description of Unknown Organism: bFGF fragment

<400> SEQUENCE: 5

Tyr Arg Ser Arg Lys Tyr Ser Ser Trp Tyr Val Ala Leu Lys Arg
1               5                  10                  15

<210> SEQ ID NO 6
<211> LENGTH: 24
<212> TYPE: PRT
<213> ORGANISM: Unknown
<220> FEATURE:
<223> OTHER INFORMATION: Description of Unknown Organism: bFGF fragment

<400> SEQUENCE: 6

Pro Ala Leu Pro Glu Asp Gly Gly Ala Ser Gly Phe Pro Pro Gly His
1               5                  10                  15

Phe Lys Asp Pro Lys Arg Leu Tyr
            20

<210> SEQ ID NO 7
<211> LENGTH: 10
<212> TYPE: PRT
<213> ORGANISM: Unknown
<220> FEATURE:
<223> OTHER INFORMATION: Description of Unknown Organism: bFGF fragment
<220> FEATURE:
<223> OTHER INFORMATION: para hydroxy phenyl propionic-amide

<400> SEQUENCE: 7

Tyr Arg Ser Arg Lys Tyr Ser Ser Trp Tyr
1               5                  10

<210> SEQ ID NO 8
<211> LENGTH: 10
<212> TYPE: PRT
<213> ORGANISM: Unknown
<220> FEATURE:
<223> OTHER INFORMATION: Description of Unknown Organism: bFGF fragment
<220> FEATURE:
<223> OTHER INFORMATION: NH(CH2)2C6H4OHp

<400> SEQUENCE: 8

Tyr Arg Ser Arg Lys Tyr Ser Ser Trp Tyr
1               5                  10

<210> SEQ ID NO 9
<211> LENGTH: 11
<212> TYPE: PRT
<213> ORGANISM: Unknown
<220> FEATURE:
<223> OTHER INFORMATION: Description of Unknown Organism: bFGF fragment
```

-continued

```
<220> FEATURE:
<223> OTHER INFORMATION: cyclo peptide

<400> SEQUENCE: 9

Gly Tyr Arg Ser Arg Lys Tyr Ser Ser Trp Tyr
 1               5                  10
```

PIGMENTORY AGENT

CROSS-REFERENCE TO RELATED APPLICATIONS

This application clams foreign priority benefits under 35 U.S.C. § 119 of Indian Patent Application No. 1051/DEL/96 and Indian Patent Application No. 1052/DEL/96, both of which were filed on May 20, 1996.

FIELD OF THE INVENTION

This invention relates to a pigmentary agent which may be used for treatment of pigmentary disorders. such as vitiligo. The preparation may also be advantageously employed as a cosmetic preparation for tanning of skin. In either instance, an exposure of the skin surface to sunlight is not necessary to cause a tanning of the skin surface. This invention also relates to a vehicle for peptides having a molecular weight of upto 1500.

PRIOR ART

It is generally known that melanocytic cells are responsible for pigmentation of the skin. Thus, a greater number of melanocytes present per/$cm^2$ of skin surface area causes a greater pigmentation. Vitiligo is a disorder caused by a deficiency or absence of functional melanocyte cells in the dermal-epidermal function.

Preparations for treatment of vitiligo are known in the art. but which were not satisfactory. Such preparations were taken orally or applied to the surface of the skin of a patient. Another treatment known in the art is the Psoralens and UVA therapy. However, such known methods required a prolonged treatement as long as one to many years. In addition, Psoralen are toxic to live and carcinogenic. Moreover, such known treatments were more often found to be ineffective.

Reference is now made to such sun screens or cosmetic preparation used for protecting the skin. Exposure to sunlight reults in tanning of skin. However, the ultra violet rays present in sunlight causes skin cancer. Thus, the sun screens known in the art were applied to prevent a penetration of the ultra violet rays.

OBJECTS OF THE INVENTION

An object of this invention is to propose a cosmetic or tanning preparation which can advantageously be employed to a skin surface without the necessity of an exposure to sunlight.

Another object of this invention is to propose a pigmetary agent for treatment of pigmentation disorders and which requires only an application to the affected skin and without the necessity of exposure to sunlight.

Yet another object of this invention is to propose a tanning preparation of pigmentary agent which requires a small concentration of the active ingredient.

A further object of this invention is to propose a tanning preparation or pigmentary agent which does not produce any harmful effects.

Yet a further object of this invention is to propose a vehicle for an active agent for a pigmentary or tanning preparation and as well as a carrier for other peptides having a molecular weight of upto 1500.

DESCRIPTION OF THE INVENTION

According to this invention there is provided a composition for treatment of pigmentation disorders and tanning applications of a skin surface without the necessity of exposure to sunlight conprising 10–50% of solvent mixed with 10–40% of glycols, 10–40% of a penetration enhancing agent and 0.5% of selective active fragments of basic fibroblast growth factor (bFGF) mixed therein.

Further, according to this invention there is provided a process for the preparation of a composition comprising mixing said solvent with said glycol at ambient temperature and pressure, adding penetration enhancing agent therein.

The present invention resides in a first aspect of a vehicle for the active agent. and a second aspect of selecting an active agent which was not hitherto known as a tanning agent, which when applied to a skin surface causes a pigmentation without an exposure to sunlight. Thus, it has now been found that the presence of the active agent in the vehicle stimulates the proliferation of melanocytic cells and thus cause a tanning of the skin surface. It has also been found that such an active agent in the particular vehicle causes a satisfactory pigmentation of the skin surface without exposure to sunlight.

In accordance with this inventior vehicle is prepared by mixing 10–50% weight by weight of solvent mixed with 10–40% of glycols and 10–40% weight by weight of penetration enhancing agent. at an ambient temperatue, preferably at a temperature around 25° C. to to this vehicle, 0.2% to 0.5% weight by weight of selective active fragment of basic fibroblast growth factor (bFGF) is added and mixed thoroughly therewith to obtain the composition of the present invention. The solvent suitable for the present composition compries alcohols selected from isopropyl alcohol, propyl alcohol or ethyl alcohol. The glycol comprises propylene glycol or polyethylene glycol. The penetration enhancing agents comprises propyl, iopropyl or ethyl myristate or propyl or ethyl stearate or propyl, isopropyl or ethyl palmitate.

The composition used for treating vitiligo and for tanning of white skin according to a preferred embodiment is herein described and illustrated in the following examples.

EXAMPLE 1

Effect of topical application of a peptide having amino acids 106–115 of bFGF SEQ ID NO: 1 or SEQ ID NO: 8 in various formulations at 0.02% on repigmenting the depigmented quinen pig ear lobes.

The controls are the ear lobe topically applied with the formulations. These are not different from the spontaneously repigmenting ear lobes. There was no difference in the speed of repigmentation irrespective of the formulation applied. The total number of control are 12 and the average extent of pigmentation at the end of 48 days is 35%. The effect of topical application of the above fragment in various formulations is evaluated for statistical significance using wilcoxan kank sum test.

TABLE 1

| COMPOSITION | ANIMAL NO. | % PIGMENTATION AFTER 48 DAYS |
|---|---|---|
| 50% isopopyl alcohol + | 48 | 95 |
| 40% propylene glycol + | 49 | 80 |

TABLE 1-continued

| COMPOSITION | ANIMAL NO. | % PIGMENTATION AFTER 48 DAYS |
| --- | --- | --- |
| 10% isopropyl myristate and + 0.02% active fragment by bFGF | 50 | 95 |
| | 36 | 40 |

The selective active fragment of basic fibroblast growth factor (bFGF) used for preparation of the solution:

1. bFGF 106–115 SEQ ID NO: 1
2. bFGF 106–120 and SEQ ID NO: 5
3. bFGF 1–24 SEQ ID NO: 6 and their modified forms SEQ ID NO: 2, SEQ ID NO 3, SEQ ID NO 1, SEQ ID NO 7, SEQ ID NO 8, SEQ ID NO 9).

Reference is now made to the active fragment, which is a peptide. The biological function is not only important in its open structure but also the 3 dimensional folding of the protein. If a protein is infected in its linear form, it would have no biological function. Thus, the protein should have a specific shape so that it is recognized by the responding cell. A molecule of substantial length cannot be applied by means of a local treatment as it cannot penetrate the stratum corneum of the skin; therefore it is necessary to use a fragment of the native protein that has the desired biological activity, yet is small enough that it is capable of penetrating the skin. The fragments identified hereabove are effective in pigmenting the dipigmented skin.

In accordance with this invention, the melanocytic cell in the vitiligo patch are either absent or not functional melanocytes. Thus, the melanocytes in perilesional area or in the outer sheath of hair follicle migrate to the vitiligo patch and start to function.

Reference is now made to the vehicle for the active agent. The description hereabove is with reference to a vehicle having a particular active agent for tanning application. However, the vehicle can advantageously be employed for other peptides as an active agent.

Peptides are known in the art which are administrated to a patient. However, such peptides could not hitherto be administrated orally or topicalily and need to be administered only in the form of an injection. The advantage of She present vehicle is that tile peptide having a molecular weight of upto 1500 can now be administered topically, and which was not hitherto possible.

Reference is made to peptides having a molecular weight of upto 1500. Though studies have yet to be effected, it is believed that the vehicle of the present invention can also be employed for topical administration of peptides having a molecular weight of more than 1500.

Accordingly, and as by way of exemplary embodiments the other peptides that can be employed are:

a) melanotropins for stimulation of melanognesis/ increased proliferation of melanocytes b) granulocyte colony stimulating factor which stermulates the defense mechanism of the body c) fusion peptides d. interleukins.

DESCRIPTION OF INVENTION WITH RESPECT TO ACCOMPANYING DRAWINGS

TABLE 2

Figure 1:
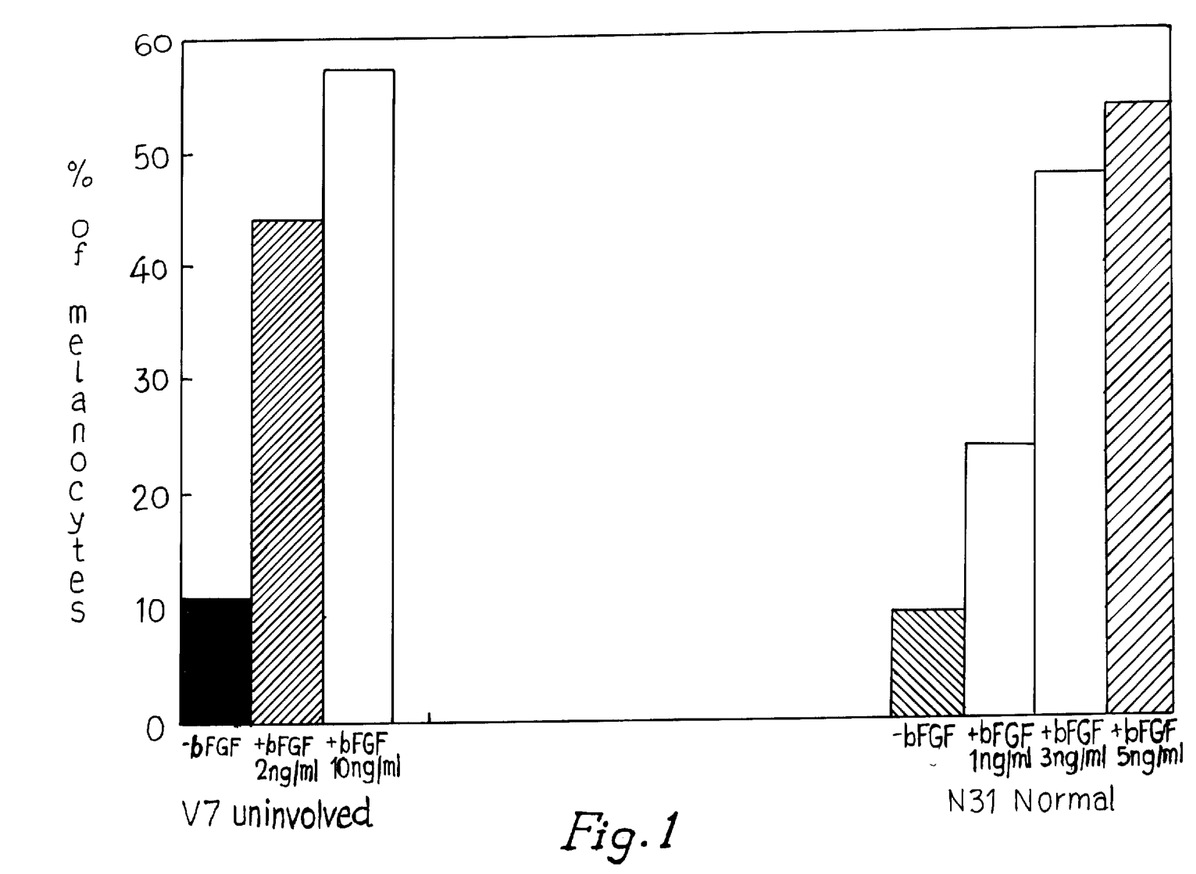
FIG. 1 shows percentage of melanocytes from an uninvolved area of a vitiligo patient V7 in response to different concentrations of bFGF compared to a normal person.
Figure 2:
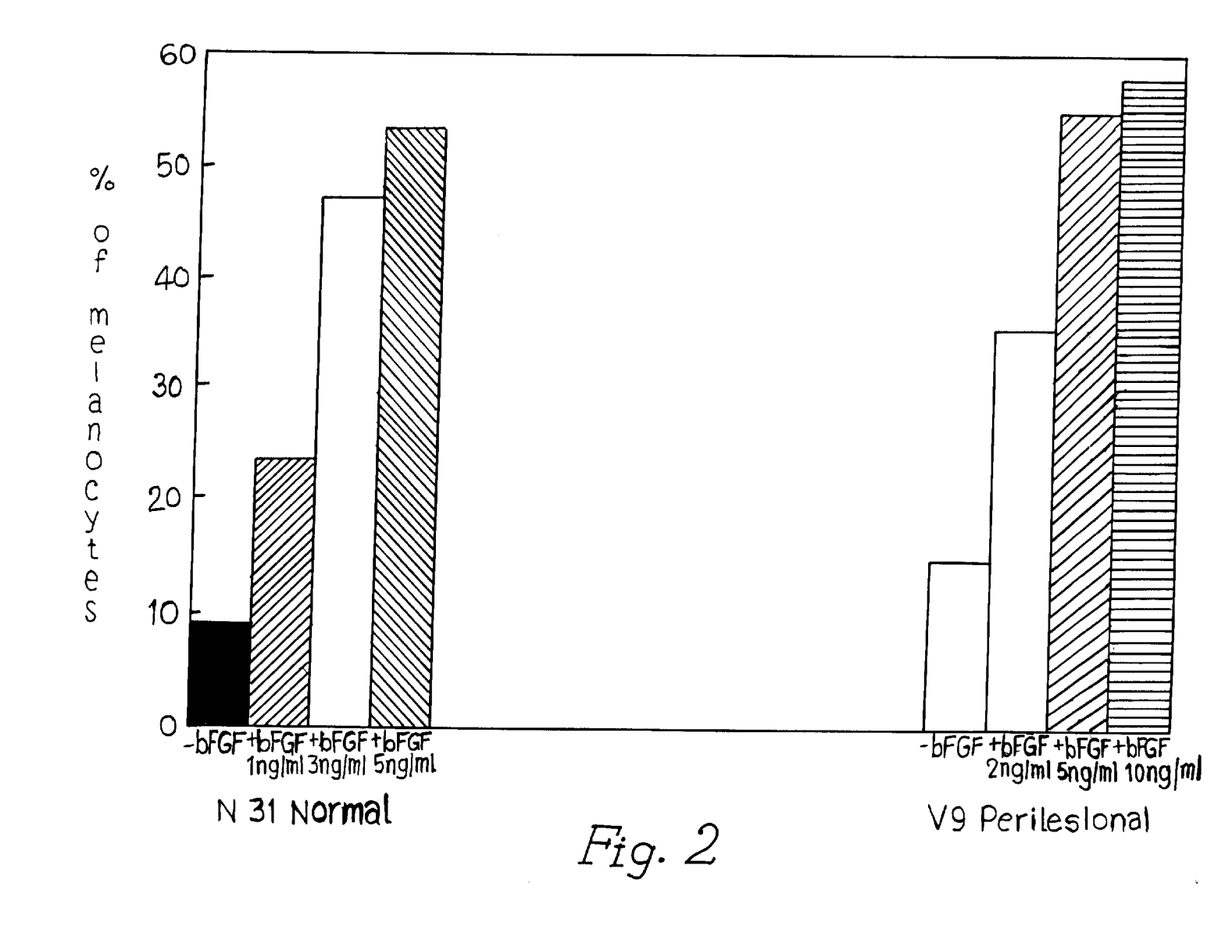
FIG. 2 shows percentage of melanocytes from the perilesional areas of a vitiligo subject V9 in response to different concentrations of bFGF compared to a normal person.
Figure 3:
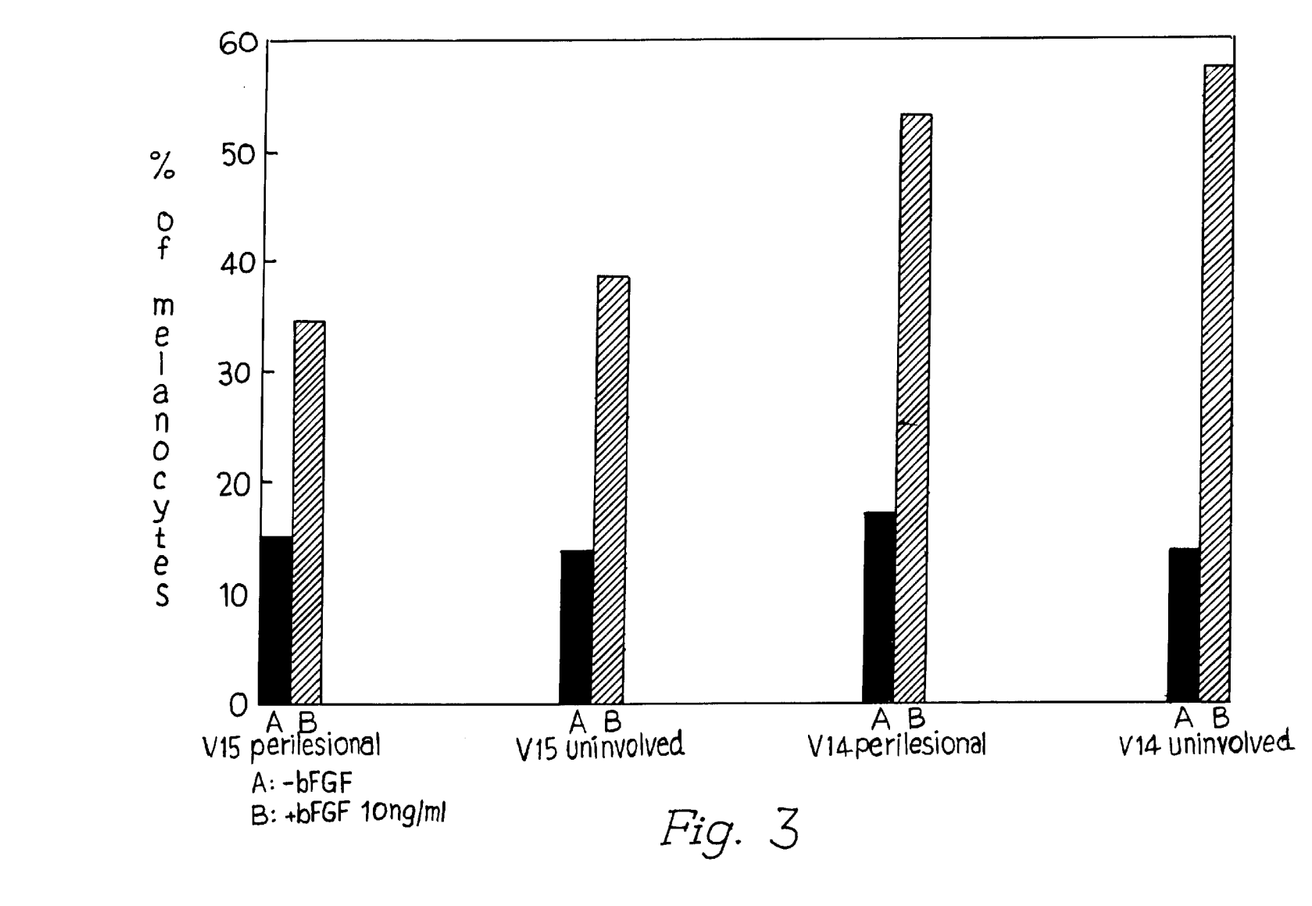
FIG. 3 shows effect of bFGF on % melanocytes in mixed cultures from the uninvolved and perilesional areas of vitiligo subjects.
Figure 4A:
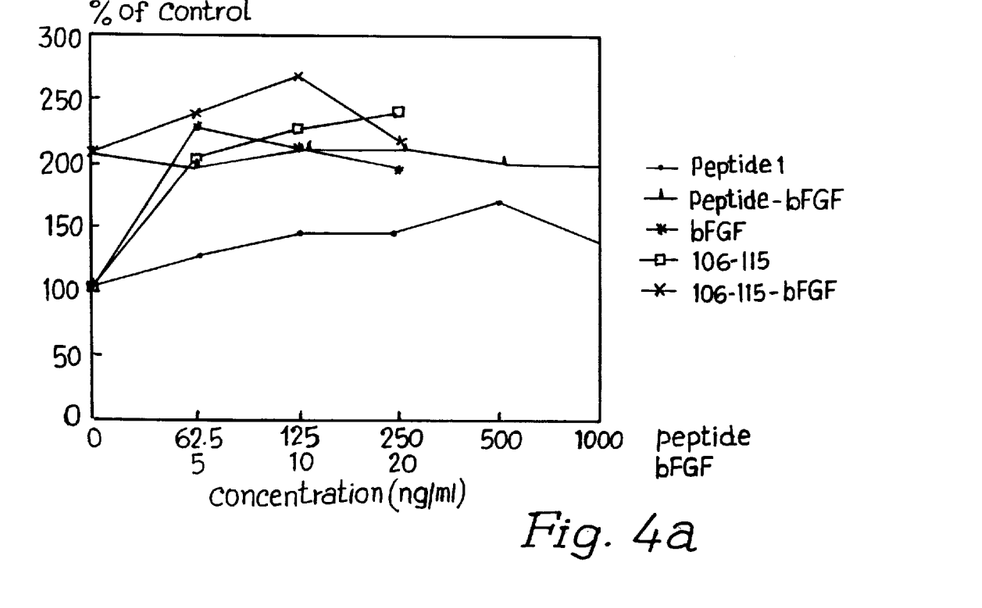
FIG. 4(a) shows the effect of fragment of 6FGF (106–115) on the melanocyte prolifeation.
Figure 4B:
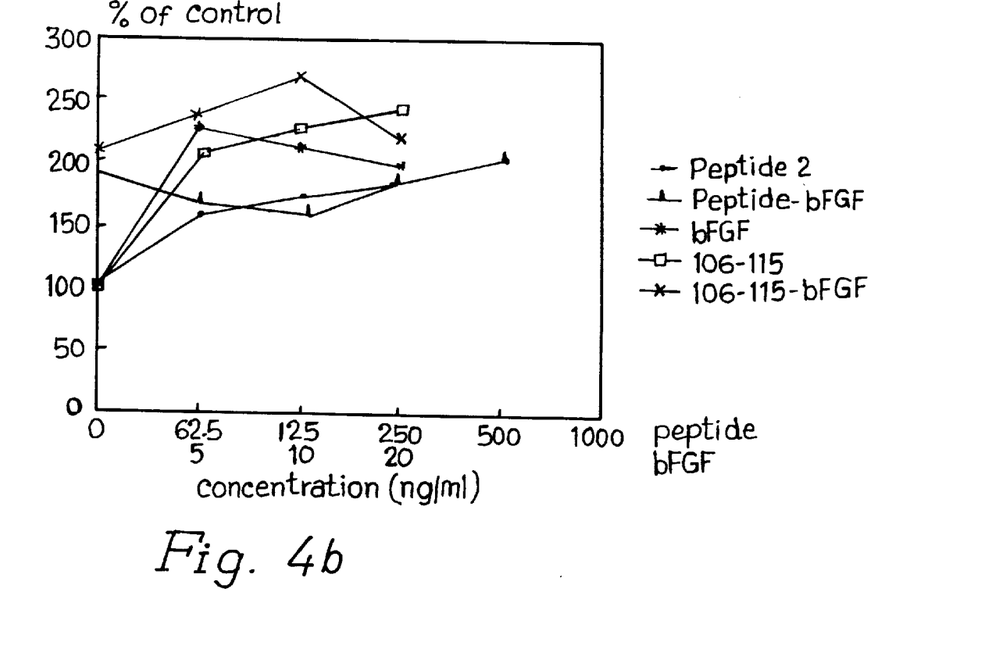
FIG. 4(b) shows the effect of active fragment of bFGF of peptide referred in Table 2 hereinbelow on the proliferation of melanocyte.
Figure 5A:
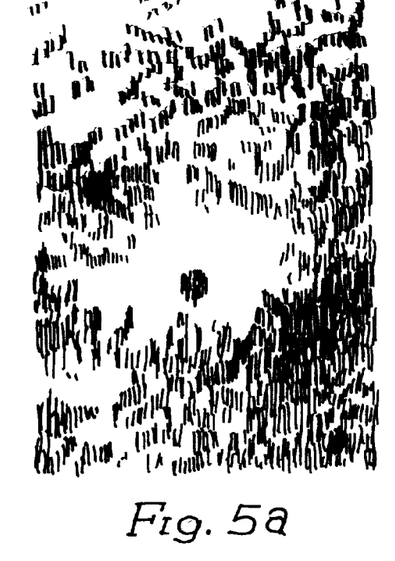
FIGS. 5(a) to (d) shows the effect of topical application of active fragment bFGF (106–115) at different concentration of 1% FIG. 5(a), 0.5% (FIG. 5b) 0.25% (FIG. 5c) and without any active fragment (FIG. 5d) on the pigmentation of skin of a Yucatan swine.
Figure 5B:
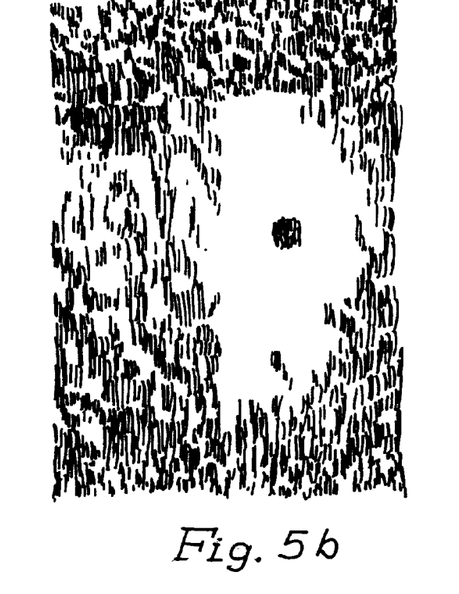
Figure 5C:
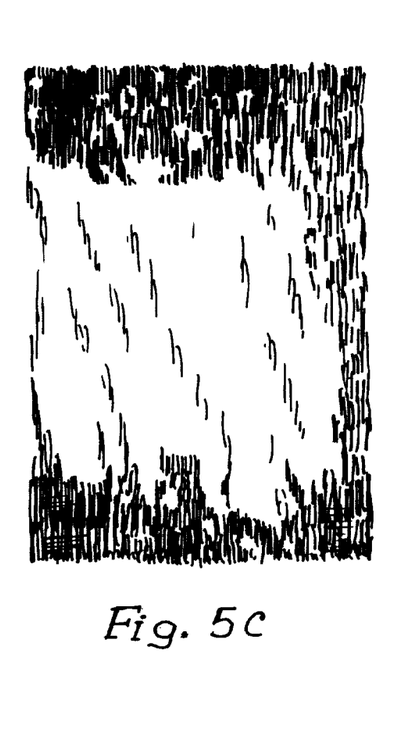
Figure 5D:
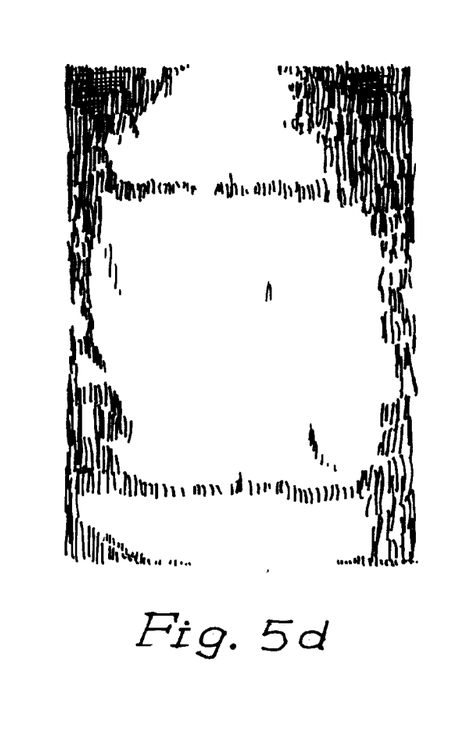
Figure 6A:
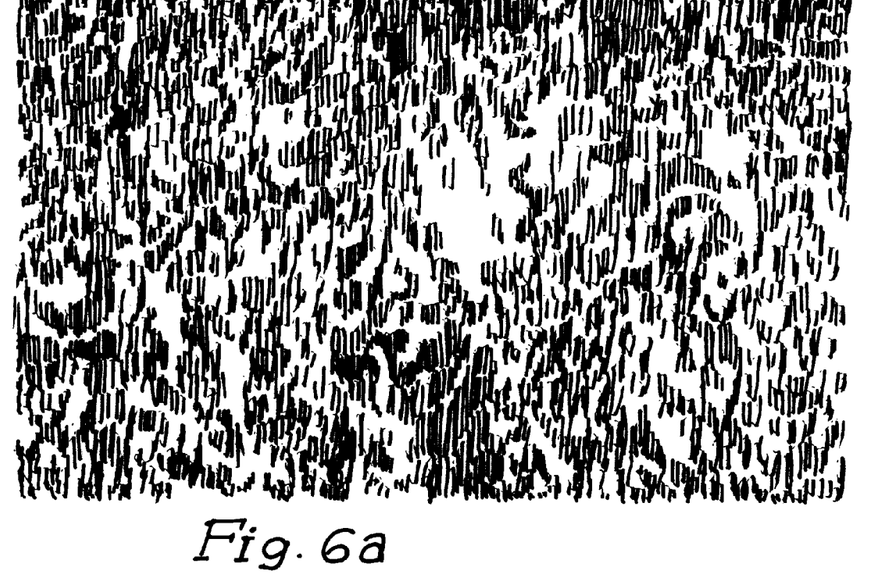
FIGS. 6A & 6B show the effect of topical application of active fragment bFGF (106–115) applied for 6 weeks and the result then observe after 20 weeks (FIG. 6A) on the extent of pigmentation of the skin of a Yucatan swine and FIG. 6B is without the fragment and FIG. 7 shows the effect.
Figure 6B:
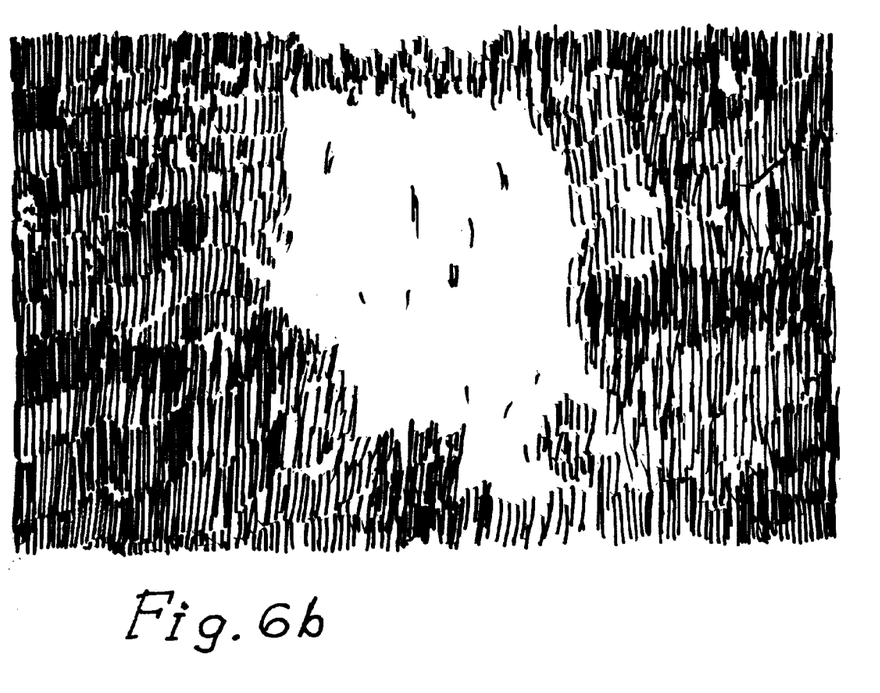
Figure 7:
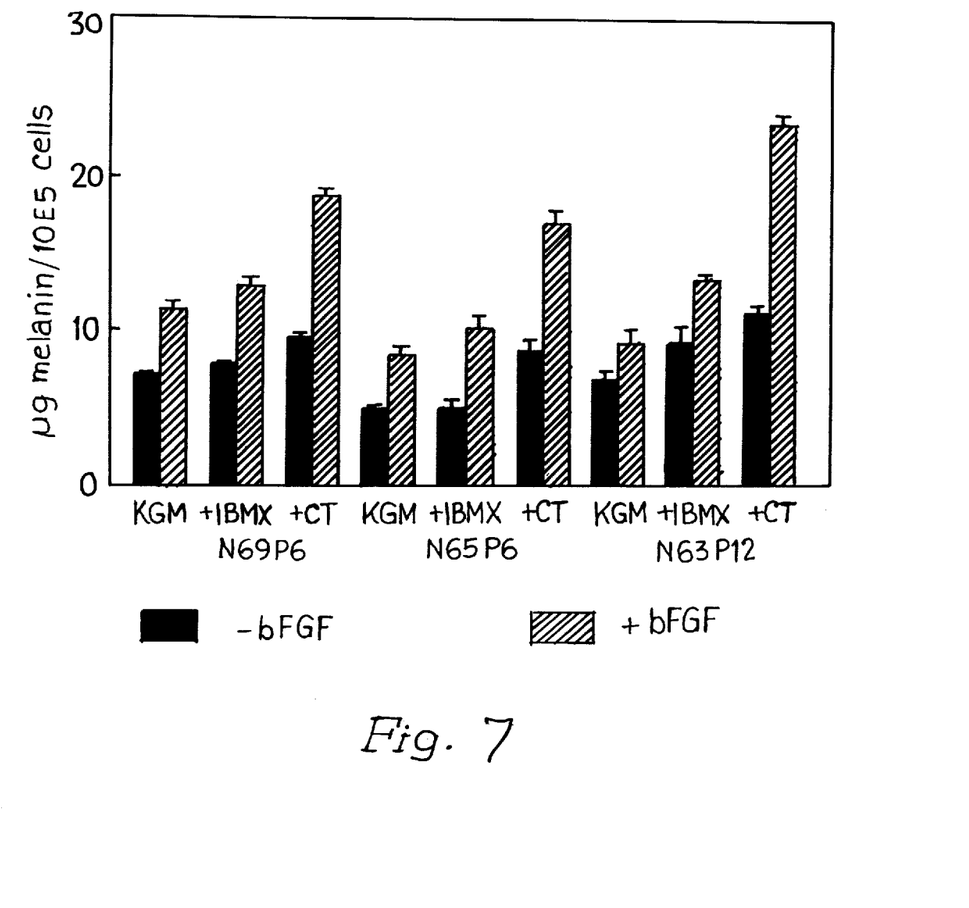

```
Sequence of the peptides tested
bFGF
    106–115 (SEQ ID NO:1)
H- Tyr  Arg  Ser  Arg  Lys  Tyr  Ser  Ser  Trp  Tyr—NH2
   106  107  108  109  110  111  112  113  114  115

Activation Replace Ser 112 by Glu: resembles phosphorylated Ser.

Peptide 1(SEQ ID NO:2):

H-Tyr  Arg  Ser  Arg  Lys  Tyr  Glu  Ser  Trp  Tyr—NH2
  106  107  108  109  110  111  112  113  114  115

Cycilsation: Make the structure more rigid. Whole bFGF is more
rigid than 106–115 peptide. More rigid: better receptor
binding. Also results in more lipophilic compound.
```

TABLE 2-continued

Peptide 2(SEQ ID NO:1):

Cyclic (Tyr Arg Ser Arg Lys Tyr Ser Ser Trp Tyr)
      106 107 108 109 110 111 112 113 114 115

Peptide 3(SEQ ID NO:9):

Cyclic (Gly Tyr Arg Ser Arg Lys Tyr Ser Ser Trp Tyr)
         106 107 108 109 110 111 112 113 114 115)

Lipophilicity: Make the peptides more penetrating. Penetration occurs probably through the hair follicle, a lipophilic environment:

Peptide 4(SEQ ID NO:7):

POHC H(CH) CO—Try Arg Ser Arg Lys Tyr Ser Ser Trp Tyr—NH2
             106 107 108 109 110 111 112 113 114 115

Peptide 5(SEQ ID NO:8):

Tyr Arg Ser Arg Lys Tyr Ser Ser Trp Tyr—NH(CH) C H OHp
106 107 108 109 110 111 112 113 114 115

What is claimed is:

1. A method of treating pigmentation disorders, comprising the step of:

applying an effective amount of a composition to skin in need of treatment, wherein the composition comprises 0.02 to 5% w/w of at least one peptide selected from a group consisting of bFGF amino acids 106–115 (SEQ ID NO 1), bFGF amino acids 106–120 (SEQ ID NO 5), bFGF amino acids 1–24 (SEQ ID NO 6), SEQ ID:2, SEQ ID:3, cyclic bFGF amino acids 106–115 (SEQ ID NO 1), cyclic bFGF amino acids 106–120 (SEQ ID NO 5), cyclic bFGF amino acids 1–24 (SEQ ID NO 6), cyclic SEQ ID:2 and cyclic SEQ ID:3.

2. A method according to claim 1, wherein the composition further comprises:

10–50% w/w of solvent;

10–40% w/w of glycols; and

10–40% w/w of at least one penetration enhancing agent.

3. A method according to claim 2, wherein the solvent is selected from a group consisting of isopropyl alcohol, propyl alcohol and ethyl alcohol.

4. A method according to claim 2, wherein the glycol is selected from a group consisting of propylene glycol and polyethylene glycol.

5. A method according to claim 2, wherein the penetration enhancing agent is selected from a group consisting of propyl myristate, isopropyl myristate, ethyl myristate, propyl stearate, isopropyl stearate, ethyl stearate, propyl palmitate, isopropyl palmitate and ethyl palmitate.

6. A method according to claim 2, wherein the composition comprises:

about 50% isopropyl alcohol, about 40% propylene glycol; and about 10% isopropyl myristate.

7. A method of tanning skin, comprising the step of:

applying a composition to skin to be tanned, wherein the composition comprises 0.02 to 5% w/w of at least one peptide selected from a group consisting of bFGF amino acids 106–115 (SEQ ID NO 1), bFGF amino acids 106–120 (SEQ ID NO 5), bFGF amino acids 1–24 (SEQ ID NO 6), SEQ ID:2, SEQ ID:3, cyclic bFGF amino acids 106–115 (SEQ ID NO 1), cyclic bFGF amino acids 106–120 (SEQ ID NO 5), cyclic bFGF amino acids 1–24 (SEQ ID NO 6), cyclic SEQ ID:2 and cyclic SEQ ID:3.

8. A method according to claim 7, wherein the composition further comprises:

10–50% w/w of solvent;

10–40% w/w of glycols; and

10–40% w/w of at least one penetration enhancing agent.

9. A method according to claim 8, wherein the solvent is selected from a group consisting of isopropyl alcohol, propyl alcohol and ethyl alcohol.

10. A method according to claim 9, wherein the glycol is selected from a group consisting of propylene glycol and polyethylene glycol.

11. A method according to claim 9, wherein the penetration enhancing agent is selected from a group consisting of propyl myristate, isopropyl myristate, ethyl myristate, propyl stearate, isopropyl stearate, ethyl stearate, propyl palmitate, isopropyl palmitate and ethyl palmitate.

12. A method according to claim 9, wherein the composition comprises:

about 50% isopropyl alcohol, about 40% propylene glycol; and about 10% isopropyl myristate.

13. A method of formulating a composition for treating pigmentation disorders or tanning skin, comprising the steps of:

intermixing 10–50% w/w of a solvent with 10–40% w/w of a glycol;

intermixing thereto 10–40% of a penetration enhancing agent; and intermixing thereto 0.02 to 5% w/w of at least one peptide selected from a group consisting of bFGF amino acids 1–24 (SEQ ID NO 6), SEQ ID:2, SEQ ID:3, cyclic bFGF amino acids 1–24 (SEQ ID NO 6), cyclic SEQ ID:2 and cyclic SEQ ID:3.

14. A method according to claim 13, wherein the solvent is selected from a group consisting of isopropyl alcohol, propyl alcohol and ethyl alcohol.

15. A method according to claim 13, wherein the glycol is selected from a group consisting of propylene glycol and polyethylene glycol.

16. A method according to claim 13, wherein the penetration enhancing agent is selected from a group consisting of propyl myristate, isopropyl myristate, ethyl myristate, propyl stearate, isopropyl stearate, ethyl stearate, propyl palmitate, isopropyl palmitate and ethyl palmitate.

17. A method according to claim 13, wherein the composition comprises:

about 50% isopropyl alcohol, about 40% propylene glycol; and about 10% isopropyl myristate.

* * * * *